US012570608B2

(12) United States Patent
Krettli et al.

(10) Patent No.: US 12,570,608 B2
(45) Date of Patent: Mar. 10, 2026

(54) COMPOUND DERIVED FROM QUINOLINE, USE OF A COMPOUND, COMPOSITION AND METHOD FOR THE TREATMENT OR PROPHYLAXIS OF A CONDITION CAUSED BY A BLOOD PARASITE

(71) Applicant: FUNDĂÇAO OSWALDO CRUZ, Rio de Janeiro (BR)

(72) Inventors: Antoniana Ursine Krettli, Belo Horizonte (BR); Mario Roberto Meneghetti, Barra de São Miguel (BR); Anna Caroline Campos Aguiar, São Carlos (BR); Wilian Augusto Cortopassi Coelho, San Francisco, CA (US); André Silva Pimentel, Rio de Janeiro (BR)

(73) Assignee: FUNDAÇÃO OSWALDO CRUZ, Rio de Janeiro (BR)

(*) Notice: Subject to any disclaimer, the term of this patent is extended or adjusted under 35 U.S.C. 154(b) by 729 days.

(21) Appl. No.: 17/640,717

(22) PCT Filed: Sep. 2, 2020

(86) PCT No.: PCT/BR2020/050351
§ 371 (c)(1),
(2) Date: Mar. 4, 2022

(87) PCT Pub. No.: WO2021/042194
PCT Pub. Date: Mar. 11, 2021

(65) Prior Publication Data

US 2022/0332685 A1 Oct. 20, 2022

(30) Foreign Application Priority Data

Sep. 6, 2019 (BR) ...................... 10 2019 018557 0

(51) Int. Cl.
*C07D 215/46* (2006.01)
*A61P 33/06* (2006.01)

(52) U.S. Cl.
CPC ............ *C07D 215/46* (2013.01); *A61P 33/06* (2018.01)

(58) Field of Classification Search
CPC ............................... C07D 215/46; A61P 33/06
See application file for complete search history.

(56) References Cited

U.S. PATENT DOCUMENTS

2006/0074105 A1 4/2006 Ware, Jr. et al.

FOREIGN PATENT DOCUMENTS

WO 2010034512 A1 4/2010

OTHER PUBLICATIONS

Aguiar et al., 8 IJP: Drug and Drug Resistance 459-464 (2018) (Year: 2018).*
Singh et al., 12(3) J. Med. Chem. 368-71 (1969) (Year: 1969).*
International Search Report w English translation and Written Opinion for PCTBR2020050351 dated Nov. 1, 26, 2020.
Read, J.A., Wilkinson, K.W., Tranter, R., Sessions, R.B., Brady, R.L., 1999. Chloroquine binds in the cofactor binding site of Plasmodium falciparam lactate dehydrogenase. J. Biol. Chem. 274, 10213 10218.
Kaschula, C.H., Egan, T.J., Hunter, R., Basilico, N., Parapini, S., Taramelli, D., Pasini, E., Monti, D., 2002. Structure-activity relationships in 4-aminoquinoline antiplasmodials. The role of the group at the 7-position. J. Med. Chem. 45, 3531-3539.
Smilkstein, M., Sriwilaijaroen, N., Kelly, J.X., Wilairat, P., Riscoe, M., 2004. Simple and inexpensive fluorescence-based technique for high-throughput antimalarial drug screening. Antimicrob. Chemother Agents. 48, 1803-1806.
Pisciotta, J.M., Coppens, I., Tripathi, A.K., Scholl, P.F., Shuman, J., Bajad, S., Shulaev, V., Sullivan Jr., D.J., 2007. The role of neutral lipid nanospheres in Plasmodium falciparam haem crystallization. Biochem. J. 402, 197-204.
Manohar, S., Khan, S.I., Rawat, D.S., 2010. Synthesis, antimalarial activity and cytotoxicity of 4-aminoquinoline-triazine conjugates. Bioorg. Med. Chem. Lett 20, 322-325.
O'Neill, P.M., Barton, V.E., Ward, S.A., Chadwick, J., 2012. 4-Aminoquinolines: chloroquine, amodiaquine and next-generation analogues. In: Staines, H.M., Krishna, S. (Eds.), Treatment and Prevention of Malaria: Antimalarial Drug Chemistry, Action and Use. Springer Basel, Basel, pp. 19-44.
Combrinck, J.M., Mabotha, T.E., Ncokazi, K.K., Ambele, M.A., Taylor, D., Smith, P.J., Hoppe, H.C., Egan, T.J., 2013. Insights into the role of heme in the mechanism of action of antimalarials. ACS Chem. Biol. 8, 133-137.
Gildenhuys, J., le Roex, T., Egan, T.J., de Villiers, K.A., 2013. The single crystal X-ray structure of beta-hematin DMSO solvate grown in the presence of chloroquine, a beta-hematin growth-rate inhibitor. J. Am. Chem. Soc. 135, 1037-1047.

(Continued)

*Primary Examiner* — Timothy R Rozof
(74) *Attorney, Agent, or Firm* — Kilpatrick Townsend & Stockton LLP

(57) ABSTRACT

Despite recent efforts to eradicate malaria worldwide, this parasitic disease is still considered a major public health problem, with a total of 219 million malaria cases and 435,000 deaths in 2017 After a decade of use, however, resistance to CQ has emerged in some locations, including Southeast Asia, South America, and the Western Pacific region, spreading progressively into malaria-endemic areas, including Africa, where increases in malaria mortality have been observed. This has led, in recent years, to the adoption of artemisinin-based combination therapies. Artemisinin-based combination therapies remain effective in most parts of the world, but recent cases of resistance in Southeast Asia call for new approaches and especially new drugs to treat malaria. Thus, the present invention features CQ analogues of Formula (I) that exhibited high activity against CQ-sensitive and CQ-resistant blood parasites and were also active in mice. The present invention also provides pharmaceutical compositions comprising the compounds of Formula (I), use of said compounds, and methods for treating conditions caused by blood parasites.

9 Claims, 6 Drawing Sheets

(56) References Cited

OTHER PUBLICATIONS

De Souza, N.B., Carmo, A.M., da Silva, A.D., Franca, T.C., Krettli, A.U., 2014. Antiplasmodial activity of chloroquine analogs against chloroquine-resistant parasites, docking studies and mechanisms of drug action. Malar. J. 13, 469.
Anna C.C. Aguiar, et al. Chloroquine analogs as antimalarial candidates with potent in vitro and in vivo activity, International Journal for Parasitology: Drugs and Drug Resistance, vol. 8, Issue 3, 2018.
Who, 2018. World Malaria Report. Available at: https://apps.who.int/iris/bitstream/handle/10665/275867/9789241565653-eng.pdf? Ua = I.
Ariey, F., Witkowski, B., Amaratunga, C., Beghain, J., Langlois, AC, Khim, N., Kim, S., Dum, V., Bouchier, C., Ma, L., Lim, P., Leang, R., Duong, S., Sreng, S., Suon , S., Chuor, CM, Bout, DM, Menard, S., Rogers, WO, Genton, B., Fandeur, T., Miotto, O., Ringwald, P., Le Bras, J., Berry, A ., Barale, JC, Fairhurst, RM, Benoit-Vical, F., Mercereau- Puijalon, O., Menard, D., 2014. A molecular marker of artemisinin-resistant Plasmodium falciparum malaria. Nature 505, 50-55.
Denizot, F., Lang, R., 1986. Rapid colorimetric assay for cell growth and survival. Modifications to the tetrazolium dye procedure giving improved sensitivity and reliability. J. Immunol. Methods 89, 271-277.
Ecker, A., Lehane, A. M., Clain, J., Fidock, D. A., 2012. PfCRT and its role in antimalarial drug resistance. Trends Parasitol 28 (11), 504-514. [0114] Egan, T.J., Hunter, R., Kaschula, C.H., Marques, H.M., Misplon, A., Walden, J., 2000. Structure-fimction relationships in aminoquinolines: effect of amino and chloro groups on quinoline-hematin complex formation, inhibition of beta-hematin formation, and antiplasmodial activity. J. Med. Chem. 43, 283-291.
Fitch, C.D., Cai, G.Z., Chen, Y.F., Shoemaker, J.D., 1999. Involvement of lipids in ferriprotoporphyrin IX polymerization in malaria. Biochim. Biophys. Minutes 1454, 31-37.
Lambros, C., Vanderberg, J.P., 1979. Synchronization of Plasmodium falciparum erythrocytic stages in culture. J. Parasitol. 65, 418-420.
Lehane, A.M., McDevitt, C.A., Kirk, K., Fidock, D.A., 2012. Degrees of chloroquine resistance in Plasmodium—is the redox system involved? Int. J. Parasitol. Drugs Drug Resist. 2, 47-57.
Olafson, K.N., Ketchum, M.A., Rimer, J.D., Vekilov, P.G., 2015. Mechanisms of hematin crystallization and inhibition by the antimalarial drug chloroquine. Proc. Natl. Acad. Know. U. S. A. 112, 4946-4951 [0125] Parhizgar, A.R., Tahghighi, A. Introducing New Antimalarial Analogues of Chloroquine and Amodiaquine: A Narrative Review. Iran J Med Sei. 2017, 42 (2), 115-128.
Talundzic, E., Okoth, S.A., Congpuong, K., Plucinski, M.M., Morton, L., Goldman, IF, Kachur, PS, Wongsrichanalai, C., Satimai, W., Bamwell, JW, Udhayakumar, V., 2015. Selection and spread of artemisinin—resistant alleles in Thailand prior to the global artemisinin resistance containment campaign. PLoS Pathog. 11, and 1004789.
Wellems, T.E., Plowe, C.V., 2001. Chloroquine-resistant malaria. J. Infect. Dis. 184, 770-776.
Yeo, S.-J., Liu, D.-X., Kim, H.S., Park, H., 2017. Anti-malarial effect of novel chloroquine derivatives as agents for the treatment of malaria. Malar. J. 16, 80.
Peters, W. "Drug resistance in Plasmodium berghei Vincke and Lips, 1948. III. Multiple drug resistance." Experimental Parasitology17.1 (1965): 97-102.
De, Dibyendu, et al. "Aminoquinolines that circumvent resistance in Plasmodium falciparum in vitro." The American journal of tropical medicine and hygiene55.6 (1996): 579-583.
Menting, John GT, et al. "The antimalarial drug, chloroquine, interacts with lactate dehydrogenase from Plasmodium falciparum." Molecular and biochemical parasitology88.1-2 (1997): 215-224.
Bray, P. G., S. A. Ward, and P. M. Oneill. "Quinolines and artemisinin: chemistry, biology and history." Malaria: drugs, disease and post-genomic biology(2005): 3-38.
Natarajan, Jayakumar K., et al. "4-N-, 4-S-, and 4-O-chloroquine analogues: influence of side chain length and quinolyl nitrogen p K a on activity vs chloroquine resistant malaria." Journal of medicinal chemistry51.12 (2008): 3466-3479.
Trager et al.; Human Malaria Parasites in Continuous Culture; Journal of Parasitology. 91(3): 484-486; American Society of Parasitologists.
Antony, Hiasindh Ashmi, et al. "In silico modeling of Plasmodium falciparum chloroquine resistance transporter protein and biochemical studies suggest its key contribution to chloroquine resistance." Acta tropica 189 (2019): 84-93.
Zishiri, Vincent K., et al. "Quinoline antimalarials containing a dibemethin group are active against chloroquinone- resistant Plasmodium falciparum and inhibit chloroquine transport via the P. falciparum chloroquine-resistance transporter (PfCRT)." Journal of medicinal chemistry 54.19 (2011): 6956-6968.

* cited by examiner

COMPOUND DERIVED FROM QUINOLINE, USE OF A COMPOUND, COMPOSITION AND METHOD FOR THE TREATMENT OR PROPHYLAXIS OF A CONDITION CAUSED BY A BLOOD PARASITE

FIELD OF INVENTION

Despite recent efforts to eliminate malaria worldwide, this parasitic disease is still considered a major public health problem, with a total of 219 million malaria cases and 435,000 deaths in 2017. The therapeutic arsenal for treating malaria is limited, due to the parasite's resistance to most of the available drugs.

The discovery, some 65 years ago, of the exceptional antimalarial properties of chloroquine (CQ) quickly paved the way for its massive use worldwide. After a few decades of use, however, resistance to CQ has emerged in some places, including Southeast Asia, South America, and the Western Pacific region. This resistance has progressively spread to malaria endemic areas, including Africa, with increases in malaria mortality worldwide. This has led, in recent years, to the adoption of artemisinin-based combination therapies. However, none of the current first-line antimalarials achieve the favorable properties of efficacy, safety, and affordability once achieved by CQ (Ecker et. al., 2012).

Artemisinin-based combination therapies remain effective in most parts of the world, however, recent cases of resistance in Southeast Asia are being reported, making the development of new approaches to treat malaria crucial.

The present invention features CQ analogues that exhibited high activity against the blood asexual stage of CQ-sensitive and CQ-resistant *Plasmodium falciparum* species and were also active in *P. berghei* infected mice.

BACKGROUNDS OF THE INVENTION

Malaria remains a major public health problem and approximately 40% of the world's population lives in malaria endemic areas distributed in 87 countries. The World Health Organization (WHO) reported a total of 219 million malaria cases and 435,000 deaths in 2017 (WHO, 2018).

Early diagnosis and successful drug treatment of infected patients are the main strategies for controlling the disease. However, a recent increase in resistance to artemisinin-based combination therapies (ACT) against *P. falciparum* in Southeast Asia poses a serious threat to malaria control and global elimination, making the search for new antimalarial drugs urgent (Ariey et al., 2014; Talundzic et al., 2015).

CQ, a 4-aminoquinoline drug, has been widely used around the world in countries where malaria is endemic, and has been the most effective, safest, and lowest cost antimalarial for many decades. CQ has a rapid onset of action, low toxicity, and is well tolerated (Wellems and Plowe, 2001).

The most accepted and discussed mechanism of action of CQ is the inhibition of hemozoin formation in the digestive vacuole of the malaria parasite (Combrinck et al., 2013; Lehane et al., 2012; Olafson et al., 2015). However, the complete understanding of the mechanism of CQ is still controversial and may include altering the pH of the digestive vacuole and inhibiting lactate dehydrogenase (Lehane et al., 2012; Read et al., 1999; Yeo et al., 2017).

The efficacy of CQ against *P. falciparum* has declined as resistant strains of the parasite have evolved, and the drug is no longer recommended for use in many parts of the world. Resistant parasites avoid the effect of CQ through a mechanism that removes CQ from the digestive vacuole. Resistance-related mutations are believed to be associated with transmembrane proteins in the parasite's digestive vacuole, including sets of critical mutations in the *P. falciparum* chloroquine resistance transporter (PfCRT) gene.

Although the *P. falciparum* species has developed widespread resistance to CQ, and cases of *P. vivax* resistance to this drug have been reported, its synthetic analogues, containing the quinoline nucleus, remain the main validated class for new drug discovery. This is because the resistance appears to be specific to each of the compounds and not related to changes in the structure of the CQ targets.

Even today, the quinoline core is still present in compounds that are being studied in clinical trials, such as ferroquine, and in approved drugs, such as amodiaquine. Furthermore, there is compelling evidence that significant and appropriate structural changes to the side chain of the CQ molecule (either by altering its length or by introducing new chemical groups) can circumvent parasite resistance to CQ (de Souza et al., 2014; Dola et al., 2017; Egan et al., 2000; Kaschula et al., 2002; Zishiri et al., 2011).

Among the existing CQ-derived compounds, we can see, for example, that different CQ derivatives have already been designed and synthesized by the prior art, as shown in the studies by Parhizgar et al. (2017). AQ-13 [Compound A] is one such analog with a shorter diamino-alkyl side chain than the alkyl chain of CQ. AQ-13 shows antimalarial activity against CQ-resistant strains.

(Compound A)

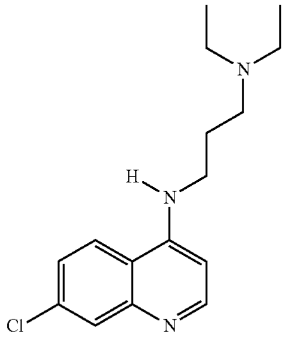

The compound has similar pharmacokinetics and mechanism of action to those found for CQ. However, in vivo studies have shown that N-deethylation of AQ-13 leads to specific changes in lipophilicity and increases the cross-resistance of this compound even more than CQ.

AQ [Compound B] is another analog of CQ, with a phenyl substituent. This is a Mannich 4-aminoquinoline base with a mechanism similar to that of CQ, and was first introduced as an alternative to CQ. Thus, AQ has been used for malaria prophylaxis and treatment against CQ-resistant strains in *P. falciparum* parasites. However, its application ended up being limited due to serious adverse effects, such as agranulocytosis and hepatotoxicity, with its long-term use. In addition, AQ has been observed to have cross-resistance with CQ.

(Compound B)

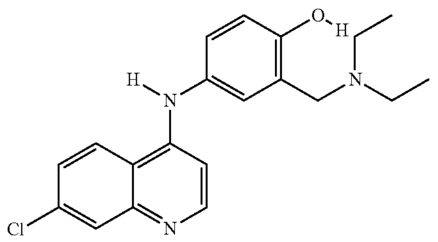

The paper by Parhizgar et. al. suggests, however, that it should be possible to maintain the length of the main side chain of the CQ and still overcome resistance to this compound, provided bulky groups are added to the side chain. One hypothesis is that the addition of bulky groups results in molecules with improved metabolic stability, allowing the molecule to have promising activity against drug-resistant parasites.

In the articles by Natarajan et al. (2008) and by De, D. et al. (1996), the authors evaluated the influence of the length of the main side chain for antimalarial activity against CQ-resistant strains of *P. falciparum*. Compound E, an analog of CQ that lacks the methyl group of the side-chain branch, was not able, however, to overcome resistance in the CQ-resistant strains FCB, Dd2, and Indochina I.

(Compound E)

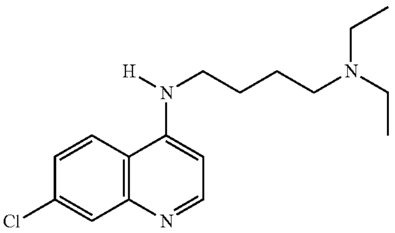

Studies by De, D. et al. (1996) also evaluated CQ analogous compounds with different main side chain lengths (C2 to C12). According to the paper, analogues with side chains of lengths ranging from 4 to 8 carbon atoms (C4-C8) were not shown to be effective against CQ-resistant strains (Indochina I). In this paper, a strategy for combating CQ resistance is suggested, which is to synthesize molecules with very short (C2-C3) or longer (>C8) major side chains.

In view of the need to provide new compounds analogous to CQ, but which can be active on resistant strains, the present inventors have developed CQ analogues with different side chains, which were prepared and tested: (i) in vitro as blood schizonticides against CQ resistant and sensitive strains of *P. falciparum*; and (ii) against *P. berghei* malaria in mice. The present inventors have also evaluated: (iii) the cytotoxicity of the compounds; (iv) their ability to inhibit β-hematin formation; and (v) their mode of binding to lactate dehydrogenase and dimeric hematin in silico. Such compounds and their procurement will be described in more detail below.

SUMMARY OF THE INVENTION

The present invention aims to provide new compounds derived from CQ. In particular, the present invention aims to provide new compounds with activity on blood parasites. More particularly, the present invention provides compounds that are active on resistant strains of malaria-causing parasites.

In a first embodiment, the present invention relates to compounds of formula (I):

Formula I

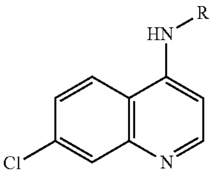

where R is $-CH_2C\equiv C(CH_2)_nN(R^1)_2$;

n is 0, 1, 2 or 3; and $R^1$ is alkyl, alkenyl, or alkynyl;

or its salts, isomers, crystals and solvates.

In this regard, the present invention also provides the use of the compounds of Formula (I) for the manufacture of a composition for the treatment of conditions caused by blood parasites.

In another aspect, the invention provides a composition comprising the presently described compounds of Formula (I).

In this regard the invention provides compositions for oral or parenteral administration of the compounds of Formula (I).

In another aspect, the present invention provides a method for treating or preventing conditions caused by blood parasites.

More specifically, the invention provides methods for treating conditions caused by parasites.

Accordingly, the present invention provides methods for treating malaria.

DETAILED DESCRIPTION OF THE INVENTION

Figure 1:
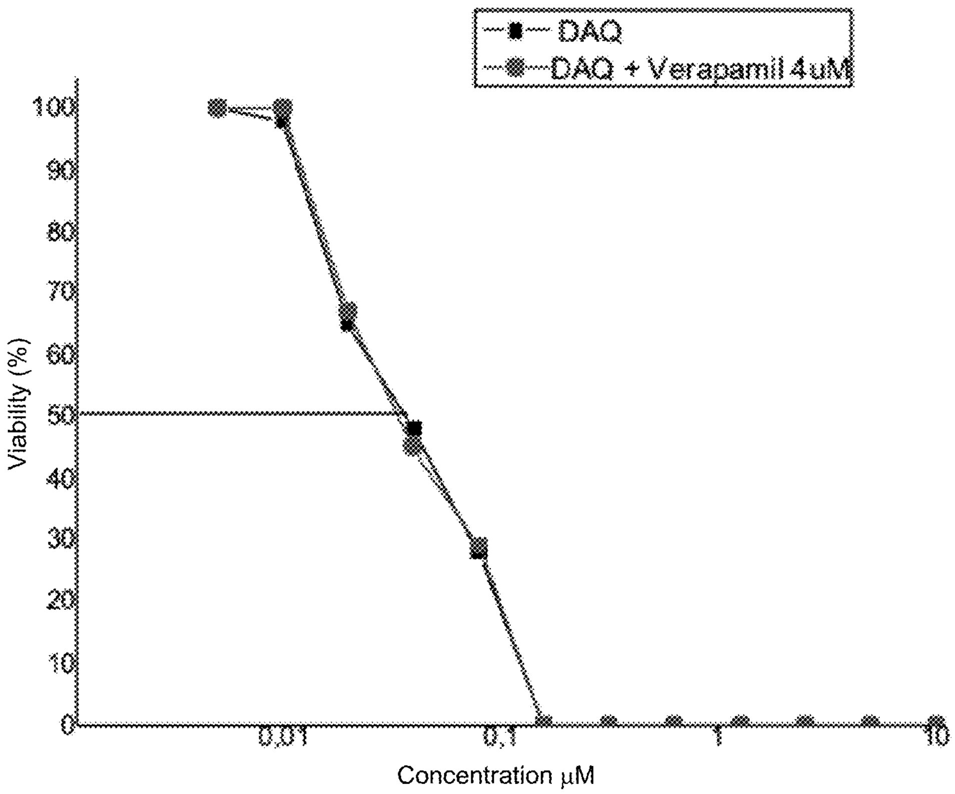
FIG. 1—Evaluation of the $IC_{50}$ of DAQ in CQ-resistant strains in the presence of verapamil.

Unless defined differently, all technical and scientific terms used herein have the same meaning as understood by someone skilled in the art to which the invention pertains. Conventional molecular biology and immunology techniques are well known to someone skilled in the art. The narrative report also provides definitions of terms to assist in the interpretation of what is described here and the claims. Unless otherwise indicated, all figures expressing quantities, percentages and proportions, and other numerical values used in the descriptive report and in claims, are to be understood as being modified in all cases by the term "about". Thus, unless otherwise stated, the numerical parameters shown in the descriptive report and in the claims are approximations that may vary, depending on the properties to be obtained.

According to the present application, the term "analogous" preferably refers to compounds in which one or more atoms or groups of atoms have been replaced by one or more different atoms or groups of atoms. Thus, the term "chloroquine analogues" refers to compounds in which one or more atoms or groups of atoms of the CQ have been replaced by one or more atoms or groups of atoms other than those normally found in the molecule.

It should be understood that the term "derivative" preferentially refers to compounds that derive from similar ones through chemical reactions, or to compounds that originate from a similar starting compound.

Thus, according to the definition in the present application, the term "analog" is to be understood as comprising and including both the definitions of the terms "analog" and "derivative" as noted above.

The present inventors have developed compounds derived from CQ and which exhibited high activity against both CQ-sensitive and CQ-resistant blood parasites.

By "blood parasites" we mean the parasites that cause malaria. More specifically, blood parasites are protozoa of the genus *Plasmodium*. The protozoa of the genus *Plasmodium* at which these compounds are targeted include, for example, *P. falciparum, P. malariae, P. ovale, P. vivax*, and *P. knowlesi*.

According to the present application, "CQ-resistant strains" are those strains that are no longer affected by or do not respond to CQ treatment. Resistant strains include, for example, *P. falciparum* K1, *P. falciparum* W2, *P. falciparum* FCR3, *P. falciparum* Indochina 1.

Surprisingly, the inventors of the present application observed that it was possible to develop new compounds derived from CQ while maintaining the length of the main side chain (C4), and maintaining the volume of the side chain, without the addition of new bulky groups.

Even more surprisingly, the present inventors have found that compounds that are derived from CQ, but have a linear side chain adjacent to the quinolinic core, exhibit a large change in the conformation of the molecule. This characteristic, allowed the compounds of the present invention to be active against CQ sensitive and resistant strains of parasites.

In the present invention, researchers have investigated the relationship between the chemical structure and antimalarial activity of CQ analogues with different side chains. To this end, four CQ analogues were prepared with different functional groups on the side chain, while maintaining three of the main points of the CQ molecular architecture:

i) the quinoline ring and its substituents;

(ii) chlorine and (iii) amino group at position 7 and 4, respectively, of the heterocyclic aromatic nucleus.

The inventors believe that these three structural features play an important role in the complexation of CQ with the toxic heme compound (ferriprotoporphyrin IX) formed during the digestion of hemoglobin by the parasite, which therefore inhibits the formation of non-toxic hemozoin crystals (Gildenhuys et al. al. 2013, O'Neill et al., 2012).

In fact, the presence of free heme causes the parasite to die. The side chain of the CQ is usually designed as a driving agent to increase the accumulation of the drug in the parasite's digestive vacuole, while the presence of the pharmacophoric portion, the quinoline ring, is important for inhibition of hemozoin crystal formation (Bray et al., 2005; Manohar et al, 2010).

Thus, the present invention relates to compounds of formula (I):

Formula (I)

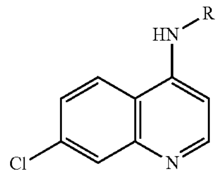

where R is $—CH_2C≡C(CH_2)_nN(R^1)_2$;

n is 0, 1, 2 or 3; and $R^1$ is alkyl, alkenyl, or alkynyl or its salts, isomers, crystals and solvates.

According to the present application, an "alkyl" is a straight or branched chain alkyl group having from 1 to 4 carbon atoms. Examples of these include a methyl group, an ethyl group, an n-propyl group, an n-butyl group, an isopropyl group, an isobutyl group, a sec-butyl group, a tert-butyl group, with preference being given to a lower alkyl group having 1 to 3 carbon atoms (methyl, ethyl, n-propyl, i-propyl group).

In the present invention, an "alkenyl" group means a straight or branched chain alkenyl group having from 2 to 4 carbon atoms and an unsaturated bond (double bond). Examples of these include an allyl group, a propenyl group, a butenyl group, and the like. The allyl group is preferred.

In this report, an "alkynyl" group means a straight or branched chain alkynyl group having 2 to 4 carbon atoms and an unsaturated bond (triple bond). Examples of these include a propargyl group and a 1-butynyl group.

The present inventors have found that the compounds of Formula (I) are active on CQ-resistant protozoan strains. One possible mechanism of *P. falciparum* resistance against CQ is through the efflux of the compound by the Chloroquine Resistance Transporter (PfCRT). However, with the addition of verapamil, a PfCRT inhibitor, the parasite again becomes sensitive to CQ.

To validate this mechanism, Dibyendu De et al. (1997) evaluated the $IC_{50}$ of CQ in a resistant strain (Indochina I) in the presence of a PfCRT inhibitor, verapamil. They observed that after PfCRT inhibition, the IC50 of CQ was effectively improved (10×).

Unlike CQ, the inventors of the present application found that the $IC_{50}$ of compounds of Formula (I) is not altered in the presence of verapamil in resistant strains (K1), suggesting that such compounds are not transported by PfCRT (FIG. 1).

The present inventors have found that the proposed mechanism of action of the compounds of Formula (I) is similar to that of CQ, that is, related to the formation of complexes with the heme group. However, unexpectedly, the present inventors have found that the linearity of the present compounds, which are inexpensive and non-toxic, can be used as an important strategy to combat the resistance mechanisms developed by the parasite.

The present inventors have also used the computational model described by Antony et al. (2019) to verify whether compounds of Formula (I) could interact with PfCRT in a similar way to CQ.

Figure 2:
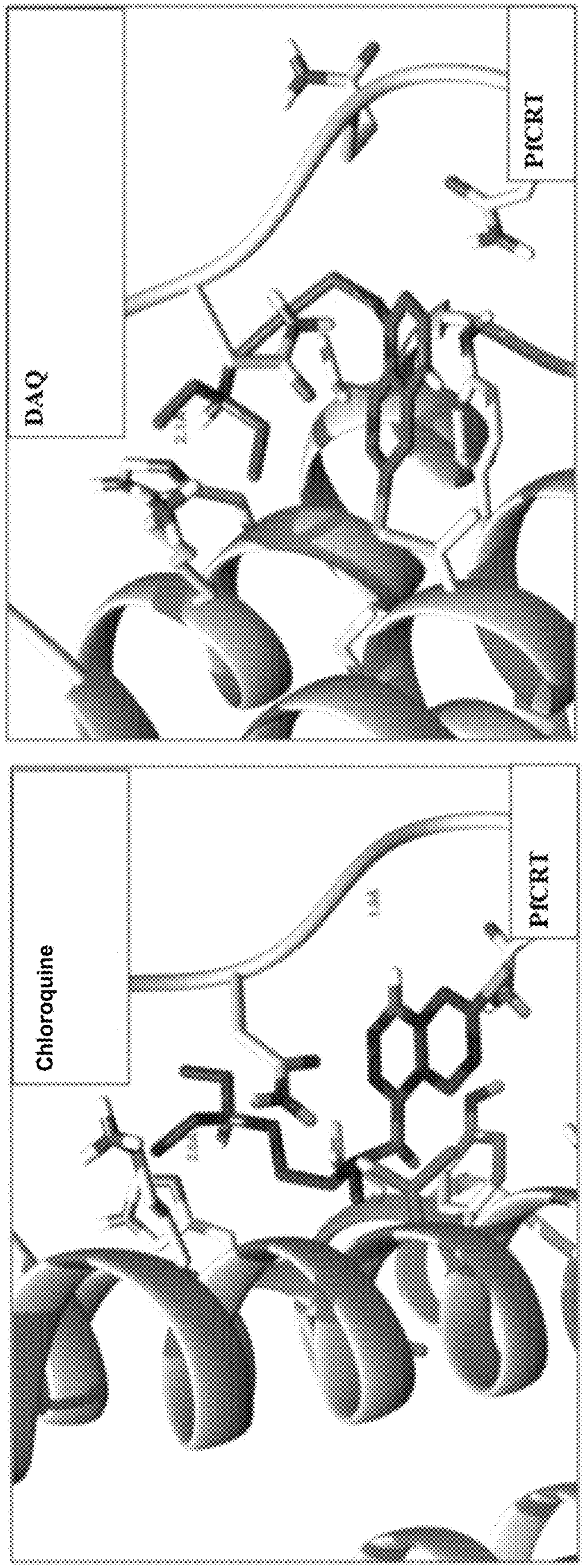
FIG. 2—Evaluation of interaction energies by the MM-GBSA method after molecular docking studies of CQ (left) and DAQ (right) on PfCRT.

In silico studies have shown that the structural differences resulting from the addition of the triple bond, present in the compounds of the invention, affect their interaction with PfCRT. Due to the presence of the triple bond, the compound does not settle within the binding site like CQ, and remains predominantly exposed to the solvent (FIG. 2).

The present inventors did not expect the compounds of Formula (I) to be active against CQ-resistant species because they have a small main side chain.

However, the inventors found that, surprisingly, even while maintaining the length of the main side chain (C4) and without the addition of bulky groups, the presence of a triple bond changes the three-dimensional conformation of the compounds of Formula (I) relative to CQ. Molecular docking studies suggest that this conformational change affects the interaction between Formula (I) compounds and PfCRT, exposing the side chain of the Formula (I) compounds to the outside of the protein and dramatically reducing the interaction energies between the molecular target and the ligand.

The present inventors therefore believe that the presence of linearity would be sufficient for compounds of Formula (I) not to be transported out of the *P. falciparum* digestive vacuole and therefore be active in CQ-resistant species.

Corroborating with the in silico studies, in vitro assays show that the $IC_{50}$ of Formula (I) compounds in CQ-resistant strains is unaffected after inhibition of PfCRT, suggesting that non-binding of the present compounds to this transporter would be the likely mechanism for overcoming resistance.

The present invention also comprises pharmaceutically acceptable salts of the compounds of Formula (I). Examples of pharmaceutically acceptable salts that can be formed by the compound of the present invention include inorganic acid salts such as hydrochloride, hydrobromide, hydroiodide, sulfate, nitrate, phosphate, diphosphate and the like, organic acid salts such as succinate, fumarate, acetate, methanesulfonate, toluenesulfonate, and the like, alkali metal salts such as sodium salt, potassium salt, and the like, alkali earth metal salts such as magnesium salt, calcium salt, and the like, ammonium salts such as ammonium salt, alkylammonium salt, and the like.

In addition, the present application also comprises solvates of the above-mentioned compound or its pharmaceutically acceptable salts. Examples of the solvent include water, methanol, ethanol, isopropanol, acetone, ethyl acetate, and the like.

As the compound of the present invention and its pharmaceutically acceptable salts show superior antiprotozoal action, they may preferably be used for the prophylaxis or treatment of protozoal infections in mammals including man, such as cattle, horse, dog, rat, mouse and the like. Examples of uses of the compounds of Formula (I) would be for the treatment of protozoan infections, with those of the genus *Plasmodium* being preferentially selected. More specifically, the compounds of the present invention can be used, for example, for the prophylaxis and/or treatment of malaria.

The present compounds, as well as their hydrate and solvate salts, can also be used as the active ingredient of a pharmaceutical agent of the present invention. The route of administration of the pharmaceutical agent of the present invention is not particularly limited, and the agent can be administered orally or parenterally. Like the pharmaceutical agent of the present invention, the compounds of Formula (I) can be directly administered to patients. Preferably, however, they should be administered as a preparation in the form of a pharmaceutical composition containing an active ingredient and at least one pharmaceutically and pharmacologically acceptable additive.

As a pharmaceutically and pharmacologically acceptable additive, for example, an excipient, disintegrant or disintegrant aid, binder, coating agent, colorant, diluent, base, solubilizer or solubilizer aid, isotonicity agent, pH regulator, stabilizer, propellant, adhesive, and the like can be used. Examples of a preparation suitable for oral administration include tablet, tablet, capsule, powder, fine granule, pellet, solution, suspension, syrup, and the like, and examples of a preparation suitable for parenteral administration include injection, intravenous fluid, inhalant powder, and the like. However, the form of preparation should not be limited only to these.

A preparation suitable for oral administration may contain, as an additive, for example, excipients such as glucose, lactose, lactose monohydrate, D-mannitol, starch, crystalline cellulose and the like; disintegrant or disintegrant aid, such as carboxymethylcellulose, starch, calcium carboxymethylcellulose, silicon dioxide and the like; binder, such as hydroxypropylcellulose, hydroxypropylmethylcellulose, polyvinylpyrrolidone, gelatin, and the like; lubricant, such as magnesium stearate, talc, and the like; base, such as hydroxypropylmethylcellulose, sucrose, polyethylene glycol, gelatin, kaolin, glycerol, purified water, hard fat, and the like.

A preparation suitable for injection or intravenous fluid may contain preparation additives such as a solubilizer or solubilizer aid capable of constituting an aqueous injection or an injection to be dissolved when in use, such as in distilled water for injection, saline, propylene glycol, and the like; isotonicity agent, such as glucose, sodium chloride, D-mannitol, glycerol, and the like; pH regulator such as an inorganic acid, organic acid, inorganic or organic base, or the like.

Although the dose of the pharmaceutical agent of the present invention should be varied, depending on the type of disease being applied, patient conditions such as age, body weight, symptom, and the like, the unit dose is generally about 1-1,000 mg of the active ingredient per oral administration. More specifically, the unit dose can be 100 to 900 mg, 200 to 800 mg, and 400 to 600 mg. In general, the above-mentioned dose can be given in one to several servings per day, or it can be given every few days. When two or more types of active ingredients are involved, the total amount must be adjusted.

The compounds of Formula (I) of the present invention may be synthesized by any methods and chemical routes known and available to one skilled in the art.

Preferably, the compounds of the present invention are synthesized in an inert atmosphere using a vacuum/inert gas line. Techniques following Schlenk's pattern can also be used in the preparation of the present compounds.

By "inert atmosphere" is meant an atmosphere consisting mostly of inert gas. According to the present invention, an "inert gas" is defined as a gas that does not react chemically under a certain set of characteristic conditions. Preferable inert gases include, for example, noble gases, and nitrogen.

In a manner particular to the present invention, the compounds of Formula (I) are synthesized in a nitrogen and/or argon atmosphere.

The present invention is described by the non-limiting examples below, which are purely illustrative. Several modifications and variations of the embodiments are evident to the one skilled in the art, without departing from the spirit and scope of the invention.

Numerous variations affecting the scope of protection of the present application are permissible. Thus, it is reinforced that the present invention is not limited to the particular configurations/embodiments described above.

EXAMPLES

Example 1

Synthesis of N-(prop-2-enyl)-7-chloroquinolin-4-amine (PCQ)

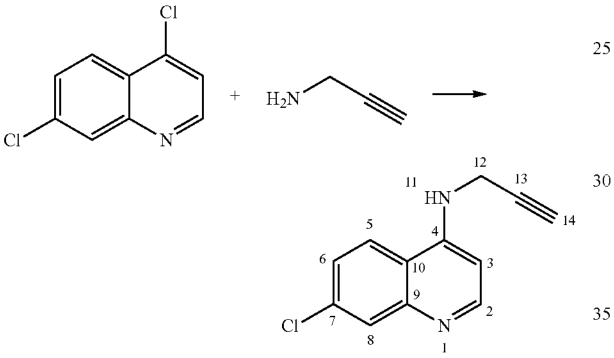

In a sealed 20 mL tube, 4,7-dichloroquinoline (1.5 g, 7.6 mmol) and phenol (7.15 g, 76 mmol) were added. After 1 h under stirring at 100° C., propargylamine (0.972 mL, 15.2 mmol) was added and the temperature was increased to 120° C. and left under stirring for another 4 h.

At the end of the period, the mixture was cooled to room temperature and a 15% aqueous Na OH solution (30 mL) was added to the reaction mixture. A yellow solid was formed, which was washed with more NaOH solution and then with water. The solid obtained was purified by column chromatography using as eluent a mixture of hexane:acetate in the ratio of 6:4 and silica gel. After the volatiles were eliminated, the product was obtained as a yellow solid. Yield: 92%.

The following characteristics were obtained for the compound:

Molecular Mass: 216.67 g/mol; HRMS-ESI for $C_{12}H_9ClN_2$ (m/z): calculated 217.0527 (M+ H+); found 217.0525 (M+ H+). Melting point: 238.1° C.

$^1$HNMR (400 MHz, MeOD): δ 2.66 (t, J=2.45 Hz, 2H, 14-CH), 3.44 (s, 1H, aminic N—H), 4.18 (d, J=2.45 Hz, 2H, 12-CH2), 6.67 (d, J=5.59 Hz, 1H, 3-Ar—H), 7.43 (dd, J=2.14 Hz and J=8.91 Hz, 1H, 6-Ar—H), 7.81 (d, J=2.22 Hz, 1H, 8-Ar—H), 8.04 (d, J=8.91 Hz, 1H, 5-Ar—H), 8.43 (d, J=5.58 Hz, 1H, 2-Ar—H).

$^{13}$CNMR (100 MHz, MeOD-d4): δ 33.01 (C-12), 73.01 (C-14), 80.42 (C-13), 100.99 (C-3), 119.09 (C-10), 124.43 (C-5), 126.57 (C-6), 127.77 (C-8), 136.65 (C-7), 149.60 (C-9), 152.23 (C-2), and 152.46 (C-4).

I.R. ($\nu_{max}$/cm$^{-1}$): 3291 (ν≡CH), 3214 (ν N—H), 3062 (ν=CH), 2921 ($\nu_{as}$ $CH_2$), 2859 ($\nu_s$ $CH_2$), 2161 (ν C≡C), 1581 (ν C═C), 1448 (δ$CH_2$), 1320 ($C_{AR}$—N), 1280 ($C_R$—N), 846 (δ=CH) e 809 (δ=CH).

Example 2

Synthesis of N-(4-(dimethylamino)but-2-enyl)-7-chloro-quinolin-4-amine (DAQ)

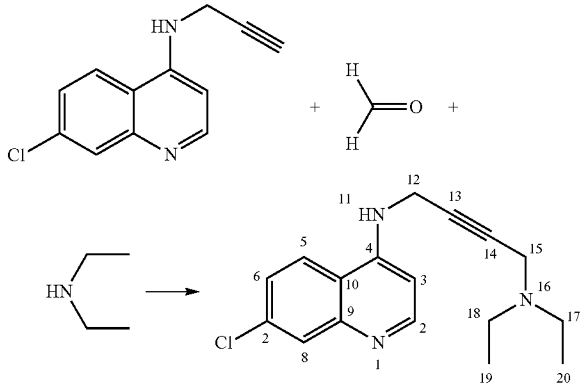

In a 50 mL round bottom flask, a solution of 50% diethylamine (3.92 mL, 18.55 mmol) and paraformaldehyde (0.450 mL, 6.01 mmol) was added. The mixture was stirred for 1 h and added to another 50 mL round bottom flask containing PCQ (1 g, 4.62 mmol), CuI (0.01158 g, 0.060 mmol) and ethanol (20 mL) which was left under reflux for 24 h. The mixture was then filtered and the liquid was dried on a rotary evaporator. The crude solid was recrystallized with ethanol/Water, recovered by filtration and dried under vacuum, resulting in a light-yellow solid. Yield: 40%.

The following characteristics were obtained for the compound:

Molecular Mass: 301.13 g/mol; HRMS-ESI para $C_{17}H_{20}ClN_3$ (m/z): calculated 302.1419 (M+ H+); found 302.1421 (M+ H+). Melting point: 153.8° C.

1>1H NMR (400 MHz, MeOD-$d_4$): δ 1.01 (t, 6H, J=7.21 Hz, 19 e 20-$CH_3$), 2.52 (q, 4H, J=7.23, 17-e 18-$CH_2$), 3.41 (t, 2H, J=1.91 Hz, 15-$CH_2$), 4.21 (t, 2H, J=1.91 Hz, 12-$CH_2$), 6.69 (d, 1H, J=5.62 Hz, 3-CH), 7.43 (dd, 1H, J=2.15 e 9.03 Hz, 6-CH), 7.81 (d, 1H, J=2.12 Hz, 5-CH), 8.04 (d, 1H, J=9.01 Hz, 5-CH) e 8.43 (d, 1H, J=5.53 Hz, 2-CH).

$^{13}$C NMR (100 MHz, MeOD-$d_4$): δ 12.19 (C-19 e C-20), 33.19 (C-12), 41.39 (C-15), 48.23 (C-17 e C-18), 78.14 (C-14), 82.36 (C-13), 101.19 (C-3), 119.12 (C-10), 124.41 (C-5), 126.53 (C-6), 127.79 (C-8), 136.61 (C-7), 149.61 (C-9), 152.22 (C-2) e 152.37 (C-4).

I.R. ($\nu_{max}$/cm$^{-1}$) 6>3237 (ν N—H), 3068 (ν=CH), 2965 e 2859 ($\nu_{as}CH_3$ e $\nu_sCH_3$), 2933 e 2815 ($\nu_{as}CH_2$ e $\nu_sCH_2$), 2161 (ν C≡C), 1579 (ν C═C), 1442 (δ $CH_2$), 1367 (δ $CH_3$), 1311 ($C_{AR}$—N) and 1238 ($C_R$—N)

Example 3

Selectivity and Activity of Four CQ Analogues Against Resistant Strains

The activity of the CQ analogues was evaluated against *P. falciparum* blood parasites [strain 3D7 a CQ-sensitive strain, and K1 a multiresistant strain], which were cultured as previously described (Trager and Jensen, 2005). Freshly synchronized sorbitol ring stages (Lambros and Vanderberg, 1979) were immediately incubated with the test compounds at various concentrations (10-0.152 μM or 1.0-0.0152 μM) previously solubilized in 0.05% dimethyl sulfoxide (DMSO) (v/v). Each test was performed in triplicate in at least two different experiments.

The results were compared with control cultures on complete medium without compounds. CQ was used in each experiment as an antimalarial control. The antiplasmodial activity of the compounds was measured by DNA labeling assay using the fluorescent probe SYBR Green (Smilkstein et al., 2004).

Briefly, plates were centrifuged at 700 g for 5 min in room temperature to remove medium, washed with PBS, and incubated for 30 min with lysis buffer solution and SYBR Green I DNA dye (1:20000). The fluorescence of the uninfected erythrocytes was considered as background. Fluorescence was measured in a fluorimeter at 485/535 nm.

The half maximum inhibitory concentration of the drug (IC50) was estimated by curve fitting using software and compared with the parasite growth in the compound-free medium.

The cytotoxicity of the CQ analogues was assessed in a human hepatoma cell line (HepG2) using cells grown in sterile 75 cm2 flasks containing RPMI-1640 medium (supplemented with 10% heat-inactivated fetal bovine serum and 40 mg/L gentamicin) under a $5\%_{CO2}$ atmosphere at 37° C. When confluent, the cell monolayer was washed with culture medium, trypsinized, dispensed into a 96-well flat-bottom plate (5×103 cells/well) and incubated for 18 hours at 37° C. for cell adhesion (Denizot and Lang, 1986).

The compounds (20 μL) at various concentrations (400-1.0 μM) were placed in the 96-well plates, incubated with the cultured cells for 24 h under a $5\%_{CO2}$ atmosphere at 37° C., and then a 3-(4,5-dimethylthiazol-2-yl)-2,5-diphenyltetrazolium bromide (MTT) solution (5 m/mL; 20 μL/well for 3 h) was used to assess mitochondrial viability.

The supernatants were carefully removed and 100 μL of DMSO was added to each well and mixed to solubilize the formazan crystals. The optical density was determined at 570 nm. Cell viability was expressed as the percentage of the control absorbance in the untreated cells after subtracting the appropriate background. Each test was performed in triplicate in at least two different experiments.

Four CQ analogues were synthesized and tested against sensitive and resistant *P. falciparum* parasites in vitro (Table 1). The compounds CEQ, PCQ and DAQ were active against the sensitive (3D7) and resistant (K1) parasites at the nanomolar dose, with IC50 ranging from 46±4 to 405±32 nM. The compound GQ was inactive at all doses tested (highest dose 10 μM).

CQ and DAQ were the most active compounds against the sensitive 3D7 strain with comparable IC50 values, but only DAQ was active against the resistant strain. The potency of the CEQ and PCQ compounds was equivalent when compared to susceptible and resistant strains. The selectivity index (SI, ratio between MDL50 and IC50) was determined using mammalian cells and the active compounds showed SI greater than 655, highlighting DAQ which demonstrated an SI almost 3 times greater than that found for CQ (Table 1).

TABLE 1

Antiplasmodial and cytotoxic activity of CQ analogues

| | IC50 (nM ± SD) P.falciparum | | $MLD_{50}$ (μM) | Selectivity index | |
|---|---|---|---|---|---|
| Structure | 3D7 | K1 | BGM-VN | 3D7 | K1 |
| 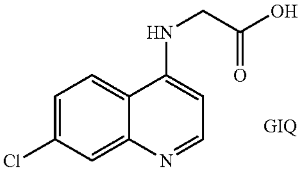 [SMILES: O=C(O)CNc1ccnc2cc(Cl)ccc12] GIQ | >10000 | >10000 | >1000 | Inactive | Inactive |
| 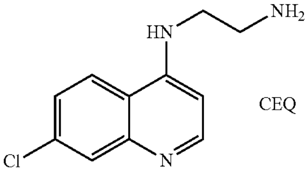 [SMILES: NCCNc1ccnc2cc(Cl)ccc12] CEQ | 273 ± 12 | 218 ± 44 | 179 ± 40 | 655 | 821 |
| 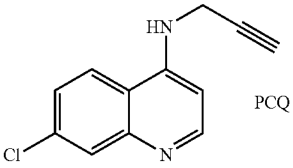 PCQ | 377 ± 14 | 405 ± 32 | 407 ± 185 | 1079 | 1005 |

TABLE 1-continued

Antiplasmodial and cytotoxic activity of CQ analogues

| Structure | IC50 (nM ± SD) P.falciparum 3D7 | K1 | MLD$_{50}$ (μM) BGM-VN | Selectivity index 3D7 | K1 |
|---|---|---|---|---|---|
| 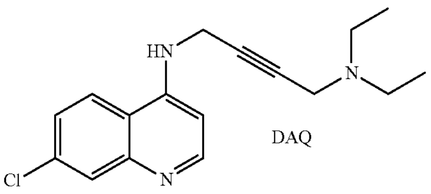 DAQ | 46 ± 4 | 50 ± 3 | 1481 ± 39 | 32195 | 29620 |
| 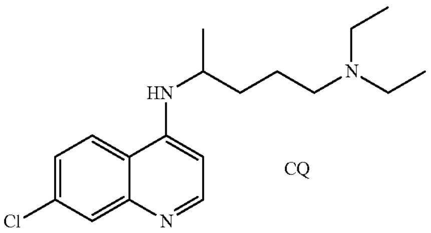 CQ | 36 ± 12 | 177 ± 20 | 420 ± 23 | 11666 | 2373 |

Figure 3:
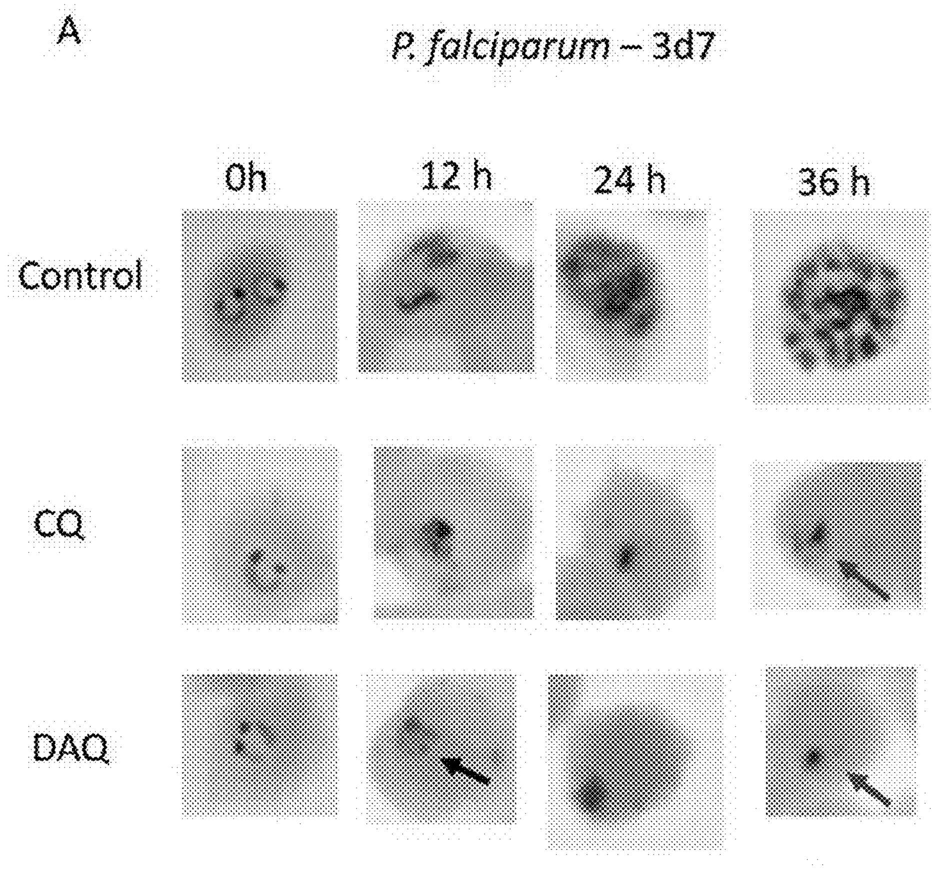
FIG. 3—Microscopy of synchronized parasites treated continuously with CQ and DAQ at 10 times the $IC_{50}$ values and with DMSO (control). Representative images from three independent experiments in CQ-sensitive *P. falciparum* 3D7.
Figure 4:
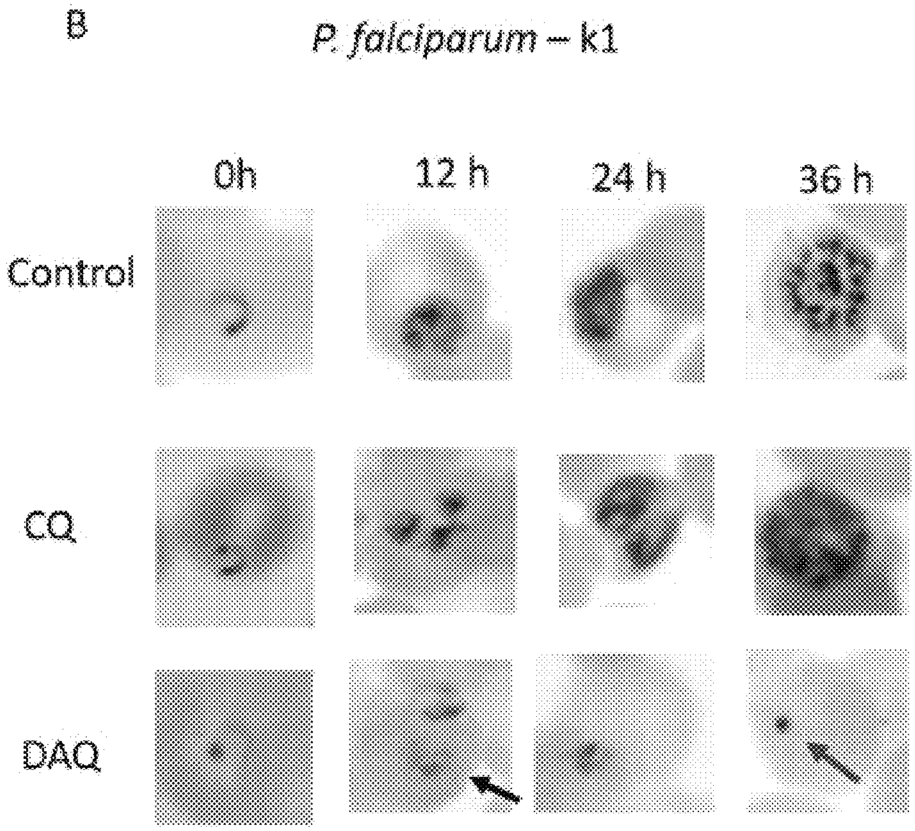
FIG. 4—Microscopy of synchronized parasites treated continuously with CQ and DAQ at 10 times the $IC_{50}$ values and with DMSO (control). Representative images from three independent experiments in CQ-resistant *P. falciparum* 3D7.
Figure 5:
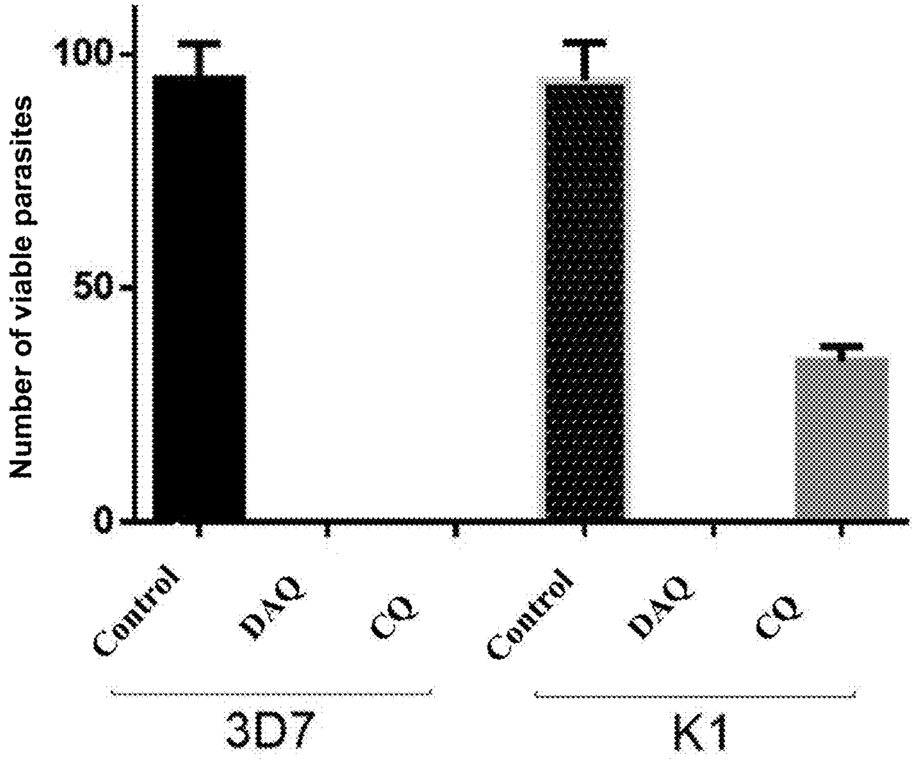
FIG. 5—Microscopy of synchronized parasites treated continuously with CQ and DAQ at 10 times the $IC_{50}$ values and with DMSO (control). Quantification of viable parasites.

The time course of inhibitory activity of the CQ analogues was also evaluated. The compounds were incubated at a concentration 10 times higher than the IC50 values obtained for the *P. falciparum* 3D7 sensitive strain with synchronized parasites. Morphological changes were then observed by microscopy after 0, 12, 24 and 36 hours after synchronization (FIG. 3). Parasites sensitive (3D7 strain) and resistant (K1 strain) to CQ were tested in parallel, and the antimalarial CQ was used as a control. All CQ analogues showed activity in the early stages of the ring against CQ-sensitive 3D7 and CQ-resistant K1 parasites, inducing changes in *P. falciparum* morphology, such as vacuolization (black arrow), between 0 and 12 h after incubation, and after 12 h incubation pyknotic nuclei (red arrow), characterizing the rapid time of action of the compounds. The CQ drug did not block complete parasite development (FIG. 4) in the resistant strain when the 10-fold IC50 for the sensitive strain was applied. These data suggest a rapid mechanism of action in which the intraerythrocytic young forms of sensitive *P. falciparum* are susceptible to the effects of Formula (I) compounds (FIG. 5).

Example 4

*P. berghei* and Antimalarial Tests in Mice

The suppression test was performed as described in Peters, 1965. A *P. berghei* NK65 strain was obtained as a donation from New York University and maintained through weekly blood draws. For the experiments, groups of up to 30 mice were inoculated i.p. with 1×105 infected erythrocytes, and kept together for about 24 h, then randomly assigned to groups of five per cage.

Mice were treated daily for three consecutive days with freshly diluted compounds in distilled water and administered orally at 50 mg/kg; control groups received the vehicle, the drug, or the antimalarial, or CQ administered at 20 mg/kg.

On days 5 to 15 after parasite inoculation, blood was taken from the tail of each mouse and used to prepare thin smears that were fixed with methanol, stained with Giemsa and examined microscopically (1000×) to determine parasitemia.

Parasite growth inhibition was determined relative to parasitemia in the untreated mice, considered to be 100% parasite growth. Compounds reducing parasitemia by >40% were considered active, between 30 and 40% partially active, and less than 30% were considered inactive. The experiments were performed twice.

The compounds DAQ and CEQ were very active reducing parasitemia by 100% by day 11 post infection and the survival of mice in these groups was significantly higher ($p<0.05$ by Mann-Whitney test) compared to the untreated control.

However, an upsurge in parasitemia could be observed on day 11 after treatment, and this phenomenon was more pronounced for the PCQ compound. Interestingly, these data corroborate with the in vitro findings, where DAQ and CEQ were the most active compounds.

The compound PCQ was active by reducing parasitemia by 70% on day 5 after infection. However, the survival of the animal was not increased compared to the untreated control. The animals treated with CQ did not show parasitemia until the last day of evaluation and survived until the last day of the experiment (Table 2).

TABLE 2

Antimalarial activity of CQ analogues in mice infected with *P. berghei* after treatment with daily doses of the compounds for three consecutive days.

| CQ Analog | Parasitemia in days (% reduction) | | | | | | |
|---|---|---|---|---|---|---|---|
| Dose (mg/kg) | 5 | 7 | 9 | 11 | 13 | 15 | Survival |
| CEQ-50 | 0.00 (100) | 0.00 (100) | 0.00 (100) | 0.00 (100) | 0.57 (94) | 4 (80) | 26 ± 6 |
| PCQ-50 | 1.04 (73) | 4.83 (10) | 5.75 (8) | 7.5 (32) | 7.0 (32) | 34.5 (0) | 17 ± 8 |
| DAQ-50 | 0.00 (100) | 0.00 (100) | 0.00 (100) | 0.00 (100) | 0.77 (92) | 3.67 (82) | 28 ± 1 |
| CQ-20 | 0.00 (100) | 0.00 (100) | 0.00 (100) | 0.00 (100) | 0.00 (100) | 0.00 (100) | >30 |
| Untreated | 3.84 | 5.42 | 6.24 | 10.8 | 10.4 | 20.2 | 19 ± 7 |

Example 5

The Antimalarial Activity of the CQ Analogues Involves the Inhibition of β-Hematin Formation The assay was performed using a lipid as a catalyst to promote crystallization (Pisciotta et al., 2007; Fitch et al., 1999). Briefly, drug stock solutions were prepared in DMSO, used at a final concentration of up to 30 mM A heme stock (10 mM) was made in DMSO and diluted to 50 mM with 100 mM sodium acetate (pH 4.8).

A 10 mM 1-monooleoyi-rac-glycerol (MOG) stock was made in ethanol and sonicated before a 50 μM heme stock was added to produce 25 μM MOG-50 μM heme in 100 mM sodium acetate (pH 4.8). The 25 μM MOG-50 μM heme solution was sonicated and added to the assay plate at 100 μL/well. The plates were incubated at 37° C. for 2 h to allow crystallization, followed by the addition of 100 μL of 200 mM sodium bicarbonate (pH 9.1) to solubilize any remaining monomeric heme. After incubation for 30 min at room temperature, the amount of solubilized monomeric heme was determined by measuring the absorbance at 405 nm.

Finally, 20 μL of 1 M sodium hydroxide was added to the plates to dissolve the crystals formed. The absorbance was read at 405 nm to determine the total amount of heme present in each well.

The inhibition of heme crystallization was determined as a function of the amount of monomeric heme that was not crystallized divided by the total amount of heme present in the test mixture. The results are expressed as IC50 values based on the percentage inhibition of β-hematin formation by compounds GIQ, CEQ, PCQ and DAQ. Each test was performed in triplicate in at least two different experiments.

Figure 6:
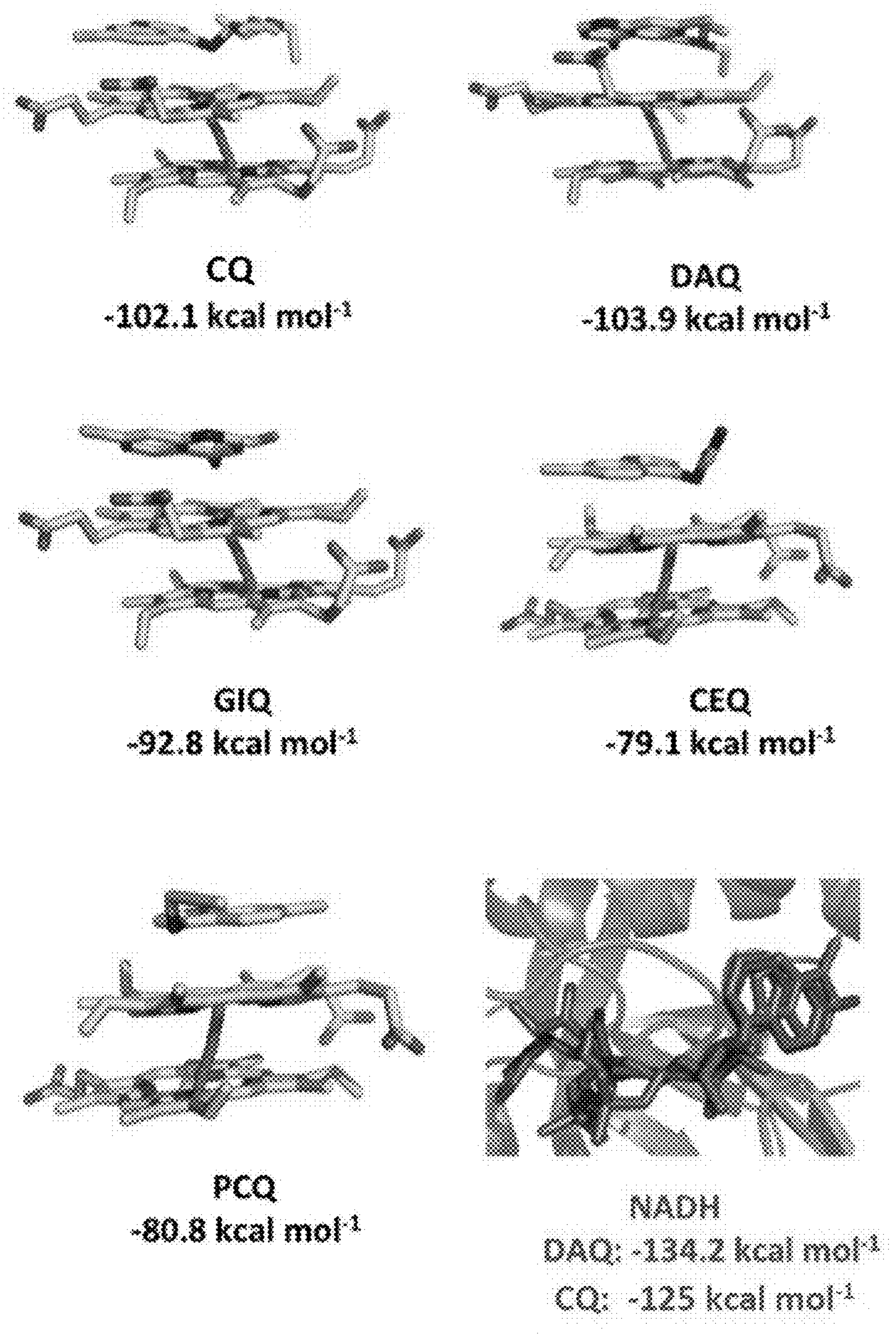
FIG. 6—Molecular docking results for CQ and its analogues DAQ, GIQ, CEQ and PCQ (top) and for dimeric heme (bottom). At the bottom of the figure, on the right, overlays of DAQ (red) and CQ (blue) for the NADH binding site (green) in PfLDH are shown.

The results showed that DAQ inhibited β-hematin formation with an IC50 value lower than that of CQ, while CEQ and PCQ inhibited β-hematin formation at concentrations 1.6- and 4-fold higher than those observed for CQ (Table 3). The GIQ compound was the least potent in β-hematin formation, as well as the least active in vitro. Similarly, docking studies showed that these compounds were able to bind parallel to dimeric heme, as observed for CQ (FIG. 6).

TABLE 3

Inhibitory Concentrations of β-hematin formation by CQ and analogues

| Analog of CQ | Inhibition of β-hematin $IC_{50}$ (mM) ± SD |
|---|---|
| GIQ | 7.6 ± 0.2 |
| CEQ | 1.2 ± 0.76 |
| PCQ | 3 ± 3 |
| DAQ | 0.15 ± 0.03 |
| CQ | 0.76 ± 0.46 |

Only DAQ and CQ showed docking energies close to −100.0 kcal mol−1 (FIG. 6 and Table 4). DAQ has a high structural similarity to CQ, with a more linear structure due to the presence of a triple bond in its aliphatic chain. Interestingly, despite these differences in the aliphatic chain, these compounds have similar anchoring positions (FIG. 6).

TABLE 4

Anchoring energies for different protonation states of CQ and its analogues DAQ, GIQ, CEQ and PCQ.

GIQ

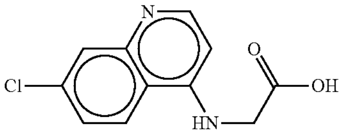

Heme: -82.9 kcal $mol^{-1}$
PfLDH: -101.6 kcal $mol^{-1}$

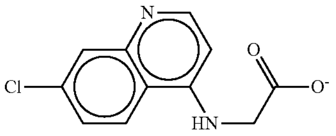

Heme: -92.8 kcal $mol^{-1}$
PfLDH: -103.8 kcal $mol^{-1}$

CEQ

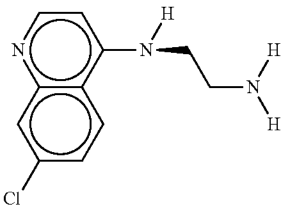

Heme: -79.4 kcal $mol^{-1}$
PfLDH: -99.4 kcal $mol^{-1}$

TABLE 4-continued

Anchoring energies for different protonation states of CQ and its analogues DAQ, GIQ, CEQ and PCQ.

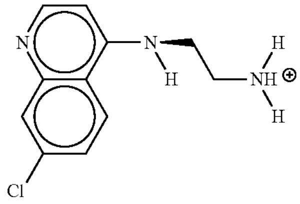

Heme: -74.5 kcal $mol^{-1}$
PfLDH: -98.2 kcal $mol^{-1}$

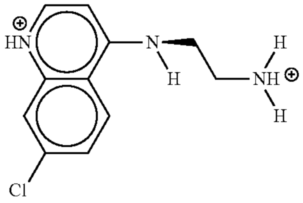

Heme: -76.5 kcal $mol^{-1}$
PfLDH: -113.6 kcal $mol^{-1}$

DAQ

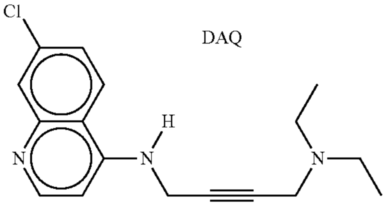

Heme: -103.9 kcal $mol^{-1}$
PfLDH: -131.2 kcal $mol^{-1}$

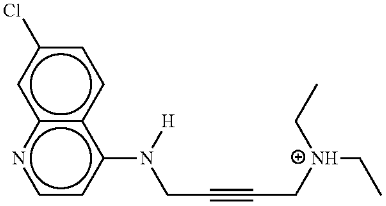

Heme: -102.2 kcal $mol^{-1}$
PfLDH: -134.2 kcal $mol^{-1}$

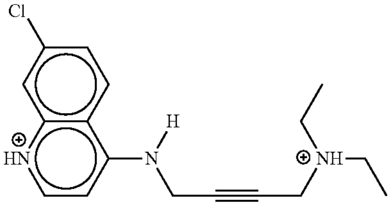

Heme: -98.3 kcal $mol^{-1}$
PfLDH: -125.5 kcal $mol^{-1}$

TABLE 4-continued

Anchoring energies for different protonation states of CQ and its analogues DAQ, GIQ, CEQ and PCQ.

CQ

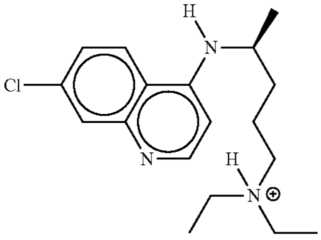

Heme: -102.1 kcal $mol^{-1}$
PfLDH: -125.4 kcal $mol^{-1}$

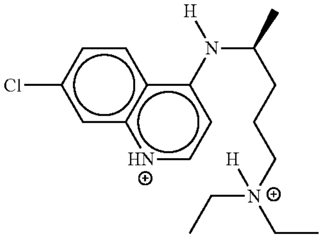

Heme: -94.5 kcal $mol^{-1}$
PfLDH: -141.9 kcal $mol^{-1}$

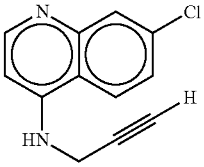

PCQ

Heme: -81.8 kcal $mol^{-1}$
PfLDH: -97.5 kcal $mol^{-1}$

Other studies have also shown that CQ binds and inhibits PfLDH, an enzyme that is crucial for parasite survival, by allowing the interconversion of lactate to pyruvate in the final stages of glycolysis, using NADH as a cofactor (Menting et al., 1997; Read et al., 1999).

The present docking results support a model where CQ binds to the NADH site at low energies (−141.9 kcal mol−1), and the quinonyl ring of CQ overlaps the aromatic rings of this cofactor (FIG. 6), which led to a model of inhibition by competition. Inhibitor-protein complexes were also constructed for GIQ, CEQ, PCQ and DAQ.

The present inventors observed that DAQ had the lowest energy among the CQ analogues (−134.2 kcal mol−1) and was also able to interact with the aromatic rings of NADH, suggestive of a mechanism similar to that of CQ. The other compounds GIQ, CEQ and PCQ showed docking energies higher than −114.0 kcal mol−1 (Table 4). Together, the docking results to dimeric heme and PfLDH show DAQ as the most promising antimalarial compound among the molecules tested in the present invention, with predicted binding energies comparable to CQ, corroborating its high selectivity index (SI=55.750) and low IC50 (0.1 mg/mL) for inhibition of β-hematin formation.

It is evident that the above examples have been presented for illustrative purposes only, and that modifications and variations thereof, obvious to those skilled in the art, are considered to be included within the scope of the present invention as defined in the following claims.

REFERENCES

Antony, H. A., Topno, N. S., Gummadi, S. N., Siva Sankar, D., Krishna, R, Parija, S. C. In silico modeling of *Plasmodium falciparum* chloroquine resistance transporter protein and biochemical studies suggest its key contribution to chloroquine resistance. Acta Trop. 2019, 189, 84-93.

Ariey, F., Witkowski, B., Amaratunga, C., Beghain, Langlois, A. C., Khim, N., Kim, S., Duru, V., Bouchier, C., Ma, L., Lim, P., Leang, R., Duong, S., Sreng, S., Suon, S., Chuor, C. M., Bout, D. M., Menard., S., Rogers, W. O., Genton, B., Fandeur, T., Miotto, O., Ringwald, P., Le Bras, J., Berry, A., Ba rale, J. C., Fairhurst, R. M., Benoit-Vical, F., Mercereau-Puijalon, O., Menard, D., 2014. A molecular marker of artemisinin-resistant *Plasmodium falciparum* malaria. Nature 505, 50-55.

Bray, P. G., Ward, S. A., O'Neill, P. M., 2005. Quinolines and artemisinin: chemistry, biology and history. Curr. Top. Microbiol. Immunol. 295, 3-38.

Combrinck, J. M., Mabotha, T. E., Ncokazi, K. K., Ambele, M. A., Taylor, D., Smith, P. J., Hoppe, H. C., Egan, T. J., 2013. Insights into the role of home in the mechanism of action of antimalarials. ACS Chem. Biol. 8, 133-137.

De, D., Krogstad, F. M., Cogswell, F. B., Krogstad., D. J. Aminoquinolines that circumvent resistance in *Plasmodium falciparum* in vitro. Am J Trop Med Hyg. 1996, 55, 579-83.

Denizot, F., Lang, R., 1986. Rapid colorimetric assay for cell growth and survival. Modifications to the tetrazolium dye procedure giving improved sensitivity and reliability. J. Immunol. Methods 89, 271-277.

de Souza, N. B., Carmo, A. M., da Silva, A. D., Franca, T. C., Krettli, A. U., 2014. Antiplasmodial activity of chloroquine analogs against chloroquine-resistant parasites, docking studies and mechanisms of drug action. Malar. J. 13, 469.

Ecker, A., Lehane, A. M., Clain, J., Fidock, D. A., 2012. PfCRT and its role in antimalarial drug resistance. Trends Parasitol 28(11), 504-514.

Egan, T. J., Hunter, R., Kaschula, C. H., Marques, H. M., Misplon, A., Walden, J., 2000. Structure-function relationships in aminoquinolines: effect of amino and chloro groups on quinoline-hematin complex formation, inhibition of beta-hematin formation, and antiplasmodial activity. J. Med. Chem. 43, 283-291.

Fitch, C. D., Cai, G. Z., Chen, Y. F., Shoemaker, J. D., 1999. Involvement of lipids in ferriprotoporphyrin IX polymerization in malaria. Biochim. Biophys. Acta 1454, 31-37.

Gildenhuys, J., le Roex, T., Egan, T. J., de Villiers, K. A., 2013. The single crystal X-ray structure of beta-hematin DMSO solvate grown in the presence of chloroquine, a beta-hematin growth-rate inhibitor. J. Am. Chem. Soc. 135, 1037-1047.

Kaschula, C. H., Egan, T. J., Hunter, R., Basilico, N., Parapini, S., Taramelli, D., Pasini, E., Monti, D., 2002. Structure-activity relationships in 4-aminoquinoline antiplasmodials. The role of the group at the 7-position. J. Med. Chem. 45, 3531-3539.

Lambros, C., Vanderberg, J. P., 1979. Synchronization of *Plasmodium falciparum* erythrocytic stages in culture. J. Parasitol. 65, 418-420.

Lehane, A. M., McDevitt, C. A., Kirk, K., Fidock, D. A., 2012. Degrees of chloroquine resistance in *Plasmodium*—is the redox system involved? Int. J. Parasitol. Drugs Drug Resist. 2, 47-57.

Manohar, S., Khan, S. I., Rawat, D. S., 2010. Synthesis, antimalarial activity and cytotoxicity of 4-aminoquinoline-triazine conjugates. Bioorg. Med. Chem. Lett 20, 322-325.

Menting, J. G., Tilley, L., Deady, Ng, K., Simpson, R. J., Cowman, A. F., Foley, M., 1997. The antimalarial drug, chloroquine, interacts with lactate dehydrogenase from *Plasmodium falciparum*. Mol. Biochem. Parasitol. 88, 215-224.

Natarajan, J. K., Alumasa, Yearick, K., Ekoue-Kovi, K. A., Casabianca, L. B., de Dios, A. C., et al. 4-N-, 4-S-, and 4-O-chloroquine analogues: influence of side chain length and quinolyl nitrogen pKa on activity vs chloroquine resistant malaria. J Med Chem. 2008, 51, 3466-79.

O'Neill, P. M., Barton, V. E., Ward, S. A., Chadwick, J., 2012. 4-Aminoquinolines: chloroquine, amodiaquine and next-generation analogues. In: Staines, H. M., Krishna, S. (Eds.), Treatment and Prevention of Malaria: Antimalarial Drug Chemistry, Action and Use. Springer Basel, Basel, pp. 19-44.

Olafson, K. N., Ketchum, M. A Rimer, J. D., Vekilov, P. G., 2015. Mechanisms of hematin crystallization and inhibition by the antimalarial drug chloroquine. Proc. Natl. Acad. Sci. U.S.A. 112, 4946-4951

Parhizgar, A. R., Tahghighi, A. Introducing New Antimalarial Analogues of Chloroquine and Amodiaquine: A Narrative Review. Iran J Med Sci. 2017, 42(2), 115-128.

Peters, W., 1965. Drug resistance in *Plasmodium berghei* Vincke and Lips, 1948. 3. Multiple drug resistance. Exp. Parasitol. 17, 97-102.

Pisciotta, J. M., Coppens, I., Tripathi, A. K., Scholl, P. F., Shuman, J., Bajad, S., Shulaev, V., Sullivan Jr., D. J., 2007. The role of neutral lipid nanospheres in *Plasmodium falciparum* haem crystallization. Biochem. J. 402, 197-204.

Read, J. A., Wilkinson, K. W., Tranter, R., Sessions, R. B., Brady, R. L., 1999. Chloroquine binds in the cofactor binding site of *Plasmodium falciparum* lactate dehydrogenase. J. Biol. Chem. 274, 10213-10218.

Smilkstein, M., Sriwilaijaroen, N., Kelly, J. X., Wilairat, P., Riscoe, M., 2004. Simple and inexpensive fluorescence-based technique for high-throughput antimalarial drug screening. Antimicrob. Agents Chemother. 48, 1803-1806.

Talundzic, E., Okoth, S. A., Congpuong, K., Plucinski, M. M., Morton, L., Goldman, I. F., Kachur, P. S., Wongsrichanalai, C., Satimai, W., Barnwell, J. W., Udhayakumar, V., 2015. Selection and spread of artemisinin-resistant alleles in Thailand prior to the global artemisinin resistance containment campaign. PLoS Pathog. 11, e1004789.

Trager, W., Jensen, J. B., 2005. Human malaria parasites in continuous culture. 1976. J. Parasitol. 91, 484-486.

Wellems, T. E., Plowe, C. V., 2001. Chloroquine-resistant malaria. J. Infect. Dis. 184, 770-776.

WHO, 2018. World Malaria Report. Disponivel em: https://apps.who.int/iris/bitstream/handle/10665/275867/9789241565653-eng.pdf?ua=1.

Yeo, S.-J., Liu, D.-X., Kim, H. S., Park, H., 2017. Antimalarial effect of novel chloroquine derivatives as agents for the treatment of malaria. Malar. J. 16, 80.

Zishiri, V. K., Joshi, M. C., Hunter, R., Chibale, K., Smith, P. J., Summers, R. L., Martin, R. E., Egan, T. J., 2011. Quinoline antimalarials containing a dibemethin group are active against chloroquinone-resistant *Plasmodium*

*falciparum* and inhibit chloroquine transport via the *P. falciparum* chloroquine-resistance transporter (PfCRT). J. Med. Chem. 54, 6956-6968.

The invention claimed is:

1. A method for treating a condition caused by a blood parasite, comprising administering to a mammal in need thereof a therapeutically effective amount of a compound of the following formula:

Formula (I)

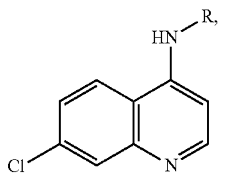

wherein:

R is $—CH_2C{\equiv}C(CH_2)_nN(R^1)_2$;

n is 0, 1, 2, or 3; and $R^1$ is $C_1$-$C_4$ alkyl, $C_1$-$C_4$ alkenyl, or $C_1$-$C_4$ alkynyl, or its salts, isomers, crystals, or solvates, wherein the blood parasite is a chloroquine resistant (CQ-resistant) blood parasite.

2. The method of claim 1, wherein:

n is 1 or 2; and $R^1$ is selected from the group consisting of methyl, ethyl, propyl, i-propyl, n-butyl, t-butyl, vinyl, allyl, and propargyl.

3. The method of claim 1, wherein:

n is 1; and $R^1$ is ethyl.

4. The method of claim 1, wherein the compound is:

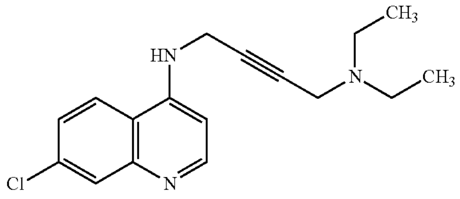 [SMILES: CCN(CC)CC#CCNc1ccnc2cc(Cl)ccc12]

or its salts, isomers, crystals, and solvates.

5. The method of claim 1, wherein the CQ-resistant blood parasite is a CQ-resistant protozoan.

6. The method of claim 5, wherein the CQ-resistant protozoan is of the genus *Plasmodium*.

7. The method of claim 6, wherein the CQ-resistant protozoan is selected from the group consisting of *P. falciparum, P. malariae, P. ovale, P. vivex*, and *P. knowlesi*.

8. The method of claim 7, wherein the CQ-resistant protozoan is selected from the group consisting of *P. falciparum* K1, *P. falciparum* W2, *P. berghei* ANKA, *P. falciparum* FCR3, and *P. falciparum* Indochina 1.

9. The method of claim 1, wherein the condition caused by a blood parasite is malaria.

* * * * *